United States Patent [19]

Nagel

[11] Patent Number: 4,826,774

[45] Date of Patent: May 2, 1989

[54] VAPOCHEROMIC DOUBLE-COMPLEX SALTS

[75] Inventor: Colleen C. Nagel, Arden Hills, Minn.

[73] Assignee: Minnesota Mining and Manufacturing Company, St. Paul, Minn.

[21] Appl. No.: 8,864

[22] Filed: Jan. 30, 1987

[51] Int. Cl.$^4$ ............................................... G01N 9/01
[52] U.S. Cl. .................... 436/106; 252/408.1; 422/55; 422/58; 422/86; 436/124; 436/126; 436/139; 436/140; 436/141; 436/142; 436/145; 436/164; 436/169
[58] Field of Search ............................ 422/55, 57, 86; 436/106, 124, 126, 139, 140, 141, 142, 145, 164, 169; 252/408.1

[56] References Cited

U.S. PATENT DOCUMENTS

| | | | |
|---|---|---|---|
| 3,197,493 | 7/1965 | Allison | 556/112 |
| 3,422,190 | 1/1969 | Ugi et al. | 558/302 |
| 3,458,542 | 7/1969 | Moore | 260/429 |
| 4,098,807 | 7/1978 | Stone et al. | 556/136 |
| 4,102,201 | 7/1978 | Trine et al. | 73/863.21 |
| 4,130,432 | 12/1978 | Wehner et al. | 106/15 |
| 4,152,118 | 5/1979 | Eller et al. | 436/122 |
| 4,271,033 | 6/1981 | Gray et al. | 252/188.31 |
| 4,350,660 | 9/1982 | Robinson et al. | 422/90 |
| 4,381,922 | 5/1983 | Frey et al. | 422/98 |
| 4,442,297 | 4/1984 | Hill et al. | 549/206 |
| 4,452,774 | 6/1984 | Jones et al. | 424/1.1 |
| 4,735,793 | 4/1988 | Jones et al. | |

FOREIGN PATENT DOCUMENTS 1209798  1/1966  Fed. Rep. of Germany ...... 558/302

OTHER PUBLICATIONS

Bonati, F.; Minghetti, G. *Inorg. Chim. Acta* 1974, 9, 95–112.
Winzenburg, M. L.; Kargol, J. A.; Angelici, R. J., *J. Organomet. Chem.* 1983, 249, 415–428.
Singleton, E.; Oosthuizen, H. E., *Adv. Organomet. Chem.*, 1983, 22, 209–238.
Bonati, F.; Minghetti, G., *J. Organomet. Chem.*, 1970, 24, 251.
Isci and Mason, *Inorg. Chem.*, 1975, 14, 913.
Mason, W. R., Gray, H. B., *J. Am. Chem. Soc.*, 1968, 90, 5721.
Isci and Mason *Inorg. Chem.* 1974, 13, 1175–1180.
Hardy, David, Kapany and Unterleitner, *Nature*, 1975, 257, 666–667.
Giuliani, Wohltjen, and Jarvis, *Optics Letters* 1983, 8, 54–56.

*Primary Examiner*—Barry S. Richman
*Assistant Examiner*—Jill Johnston
*Attorney, Agent, or Firm*—Donald M. Sell; Walter N. Kirn; Lorraine R. Sherman

[57] ABSTRACT

Articles comprise transition metal double-complex salts which contain arenyl isonitrile ligands derivatized with long aliphatic chains, the cation being a tetrakis isonitrile platinum ion and the anion being a tetracyanopalladate ion. These double-complex salts exhibit novel vapochromic effects and are useful as personal and badge monitors, threshold monitors, optical waveguide sensors, chemical field effect transistors, and in related monitoring applications.

21 Claims, No Drawings

VAPOCHROMIC DOUBLE-COMPLEX SALTS

FIELD OF THE INVENTION

This invention relates to articles comprising transition metal-containing double-complex salts. These salts exhibit vapochromic properties and are useful in chemical, physical, and environmental monitoring applications.

DESCRIPTION OF THE BACKGROUND ART

Historically, complexes containing isonitrile ligands have been limited to those containing the few commercially available isonitriles like t-BuNC, PhNC, or the readily synthesized and purified isonitriles like MeNC, EtPhNC, MeOPhNC, MePhNC wherein tBu=tertiary butyl, Ph=phenyl, Et=ethyl, and Me=methyl. For a review see: Bonati, F.; Minghetti, G. *Inorg. Chim. Acta* 1974, 9, 95–112. Only recently have complexes containing more 'exotic' isonitriles been studied (Winzenburg, M. L.; Kargol, J. A.; Angelici, R. J. *J. Organomet. Chem.* 1983, 249, 415–428).

Salts of the type $[L_4M][M'X_4]$ are known as double-complex salts, i.e. the salt is composed of two metal-containing complex ions. Salts where L is often an amine or isonitrile, X is a halide or cyanide, and both M and M' are platinum have been known for many years. For a recent review of metal isocyanide complexes see: Singleton, E., Oosthuizen, H. E. *Adv. Organomet. Chem.* 1983, 22, 209–238. Both the cation and anion comprising these complexes have square-planar geometries and often assume structures in which the ions form mixed stacks; the resulting metal-metal interactions cause these solids to be intensely colored despite the fact that the component ions absorb below 350 nanometers(nm) (Bonati, F., Minghetti, G., *J. Organomet. Chem.* 1970, 24, 251; Isci and Mason, *Inorg. Chem.* 1975, 14, 913; Mason, W. R., Gray, H. B.. *J. Am. Chem. Soc.* 1968, 90, 5721). A study of the optical properties of these complexes is reported by Isci and Mason, (*Inorg. Chem.* 1974, 13, 1175–1180).

Simple salts having cations of the type $[(RNC)_4M]^{n+}$ where M includes radioactive isotopes of Rh(n=1) and Ni, Pd, or Pt(n=2) are described in U.S. Pat. No. 4,452,774 for use as diagnostic agents for labeling living cells. U.S. Pat. No. 4,271,033 describes binucleating biisocyanide complexes of Rh, Pt, Pd, Ni useful as catalysts. Isonitrile or isocyanide complexes of copper, described in U.S. Pat. No. 3,197,493, are useful as intermediates in the preparation of isonitriles.

U.S. Pat. No. 4,130,432 claims alkyl tin tetracyanometallates as biocides. Double salts of tetracyanoaurate useful for plating gold alloys are described in U.S. Pat. No. 3,458,542.

Use of transition metals in sensors is known in the art; transition metal complexes used have predominantly been phthalocyanine or porphyrin derivatives as seen, for example, in U.S. Pat. No. 4,381,922 and U.S. Pat. No. 4,350,660.

A patent on organometallics dealing with sensors is U.S. Pat. No. 4,152,118 which claims a phosphine copper complex which functions as a sulfur dioxide indicator. U.S. Pat. No. 4,442,297 describes manganese complexes which coordinate hydrogen, carbon monoxide, oxygen, sulfur dioxide, and alkenes and can be used as indicators or gas separators.

Methods have been devised to chemically trap and analyze vapors as taught in U.S. Pat. No. 4,102,201; however, such methods do not allow for immediate (real time) indication of organic vapors.

Sensing of gases using optical waveguide gas sensors was first reported in 1975 by Hardy, David, Kapany, and Unterleitner, (*Nature* 1975, 257, 666–667). State of the art optical waveguide sensors often utilize chemically reactive dyes which, unfortunately, often have limited shelf life, may undergo irreversible chemical changes and are chemically specific as described by Giuliani, Wohltjen, and Jarvis, (*Optics Letters* 1983, 8, 54–56, and references cited therein).

SUMMARY OF THE INVENTION

Briefly, the present invention provides an article comprising a transition metal double-complex salt comprising four arenyl isonitrile ligands, at least one of which, and preferably all, contains a long chain aliphatic group, the salt having two metal-containing complex ions, the cation being a tetrakis isonitrile ligand-containing platinum ion and the anion being a tetracyanopalladate ion. Both the cation and anion in the double-complex salts have a $d^8$ electronic configuration (8 electrons in the "d" orbital) or are capable of forming a square planar configuration. The complex salts are water and air stable.

The unexpected and novel solid state property of vapochromism, which is not present in shorter aliphatic chain homologs, is obtained as a result of incorporation of long aliphatic chains in the isonitrile ligand of the mixed transition metal double-complex salts of this invention.

Double-complex salts of the present invention are vapochromic and highly colored as well as fluorescent in the visible spectrum; thus, visual as well as instrumental and optical monitoring of vapors is possible.

The complex salts of the invention are useful as personal and badge monitors, threshold monitors, optical waveguide sensors, chemical field effect transistors, and in related monitoring applications, even when the monitors are wet or subjected to moisture. In all cases, at least a portion of the solid complex is not overcoated by any other material.

In contrast to the background art, the present invention teaches the immediate (real time) detection of vapors by visual, optical or other sensing methods, devices, or combinations thereof. Furthermore, reversibility of color and fluorescence changes of the compounds of this invention in the absence and presence of vapors make the complex salts suitable for continuous vapor monitoring and for repeated use.

The vapochromic mixed transition metal isonitrile-containing double-complex salts of the invention (see formula I below) constitute new compounds; synthesis and properties of such salts, it is believed, have never been reported. These salts which are useful in thermochromic applications, dispersions thereof, and method of their preparation are the subject of U.S. Ser. No. 07/009,366, filed the same date as this application.

The complex salts of the invention are preferably prepared by providing stoichiometric amounts of bis-acetonitrile platinum dihalide, the chosen isonitrile, and a salt of $[Pd(CN)_4]^{2-}$ in an organic liquid with a small amount of water added if desired to dissolve the Pd salt, stirring the reaction mixture at room temperature for an appropriate length of time, and isolating the desired product. Alternatively, instead of bis-acetonitrile platinum dihalide, other types of ligand-containing platinum dihalides may be used.

Preparation of the tetracyanopalladate double-complex salts via a non-ionic platinum compound (see, for example, Eq. 5 below) provides the preferred route to the novel mixed transition metal salts. Use of a non-ionic complex as the cation precursor ensures that no residual tetrahalo-substituted transition metal ions will contaminate the desired product. This often occurs when the standard synthetic route, based on displacement of halide from tetrahalometallates, is used.

Compounds of this invention are inert to ambient conditions such as light, air, and humidity, yet have broad analytical applicability by exhibiting color and other physical changes such as changes in fluorescence or index of refraction. These novel compounds, articles, and composites containing them are useful as chemical detectors and sensors by using visual, optical (such as fluorescence or absorption), and other instrumental means.

In this application:

"aliphatic" means the monovalent group remaining after removal of a hydrogen atom from a linear, branched, or cyclic hydrocarbon having 1 to 20, preferably 5 to 18, carbon and optional heteroatoms and includes such groups as alkyl, alkenyl, and alkynyl group; these groups can be interrupted by 1 to 4 unitary heteroatoms selected from S, N, and O;

"alkenyl" means the monovalent group remaining after removal of a hydrogen atom from a linear or branched chain hydrocarbon having 2 to 20 carbon and optional heteroatoms which contains at least one double bond; the alkenyl group can be interrupted by 1 to 4 unitary S, N, and O atoms;

"alkynyl" means the monovalent group remaining after removal of a hydrogen atom from a linear or branched chain hydrocarbon having 2 to 20 carbon and optional heteroatoms which contains at least one triple bond; the alkynyl group can be interrupted by 1 to 4 unitary S, N, and O atoms;

"aryl" means the monovalent group remaining after removal of one hydrogen atom from an aromatic or heteroaromatic compound which can consist of one ring or two fused or catenated rings having 5 to 18 ring atoms which can optionally include 1 to 3 unitary heteroatoms selected from S, N, and O;

"arenyl" means the monovalent group remaining after removal of a hydrogen atom from the aliphatic or aryl portion of a hydrocarbon containing both aliphatic and aryl groups having 7 to 26 carbon and optional heteroatoms, wherein the aliphatic portion of the arenyl group can be 1 to 4 unitary S, N, and O atoms; preferably the aryl portion of the arenyl group is attached to the isonitrile ligand; thus, arenyl includes among other groups, alkaryl;

"alkaryl" means the monovalent group remaining after removal of a hydrogen atom from the aryl portion of a hydrocarbon containing both alkyl and aryl groups having 7 to 26 carbon and optional heteroatoms and the alkyl portion can optionally be interrupted by unitary heteroatoms (wherein the heteroatoms are up to 4 unitary S, N, and O atoms);

"vapochromism" means a change in color or absorbance in the electromagnetic spectrum, preferably in the visible portion of the spectrum, induced by vapors of organic compounds which have vapor pressures at room temperature of at least 0.001 torr.;

"fluorescent" means the immediate emission of light (UV, visible, or near IR) from a molecule after it has absorbed electromagnetic radiation;

"monitor" means any article, item, or means which is used to detect, sense, indicate, test, police, and the like, an existing condition or change in existing conditions; and "dispersion" means a distribution of finely divided particles in a liquid medium that show no substantial tendency to settle in 20 minutes as determined by percent transmission mesurements at 400 nm; and "real time" means the results of the on-going monitoring are immediately available.

DETAILED DESCRIPTION

This invention provides articles comprising transition metal double-complex salts in which the the salt is composed of two metal-containing complex ions; the cation is a tetrakis isonitrile platinum ion and the anion is tetracyanopalladate as described by the formula:

$$[(LC_6H_4NC)_4Pt]^{2+}[Pd(CN)_4]^{2-} \qquad \text{I}$$

wherein L can be independently selected from aliphatic groups and hydrogen with the proviso that:

for at least one L, preferably two, three, or four L's, the total number of carbon and heteroatoms in L is 8 to 20 wherein the heteroatoms are 0 to 4 unitary heteroatoms or heteroatom-containing functional groups, that L contains a chain of at least 6, preferably 8, linear catenated carbon atoms; the chain being attached to the $C_6H_4$ ring which has an isonitrile group in a position ortho, meta, or para to the chain; preferably L is in the para position to the isonitrile group;

as noted above, L optionally can contain 1 to 4 unitary heteroatoms and divalent functional groups selected from

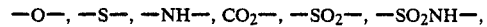

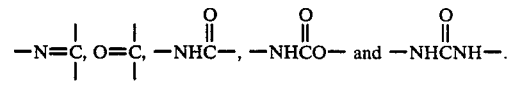

Preparation of the tetrakisisonitrile metal cation, wherein all L are the same has been accomplished by two routes: displacement of halide like chloride from commercially available tetrahalometallates (Miller, J. S.; balch, A. L. *Inorg. Chem.* 1972, 11, 2069) or by alkylation of commercially available tetracyanometallates (Treichel, P. M.; Knebel, W. J.; Hess, R. W. *J. Am. Chem. Soc.* 1971, 21, 5424) as shown below.

Displacement:

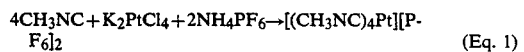

(Eq. 1)

Alkylation:

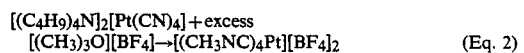

(Eq. 2)

The displacement method may be used if L's are to be different by using an appropriate mixture of the different isonitrile ligands. Practical alkylation is limited by the number of commercially available alkylating agents.

Cyanometallate double-complex salts are sometimes made in one step as well (Isci, H., Mason, W. R. *Inorg.*

Chem. 1974, 13, 1175), but contamination with tetrahalometallate can be a problem (Keller, H. J., Lorentz, R. J. *Organomet. Chem.* 1975, 102, 119–122; and *Z. Naturforsch. B.* 1976, 31B, 565–568).

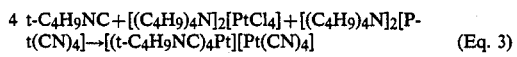

$$4\ t\text{-}C_4H_9NC + [(C_4H_9)_4N]_2[PtCl_4] + [(C_4H_9)_4N]_2[Pt(CN)_4] \rightarrow [(t\text{-}C_4H_9NC)_4Pt][Pt(CN)_4] \quad (Eq.\ 3)$$

Metathesis can also be employed if the salts of the metal-containing cation and anion have been previously isolated (Isci, H.; Mason, W. R. *Inorg. Chem.* 1974, 13, 1175). Such a method should also be suitable for formation of mixed-metal complex salts.

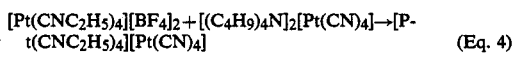

$$[Pt(CNC_2H_5)_4][BF_4]_2 + [(C_4H_9)_4N]_2[Pt(CN)_4] \rightarrow [Pt(CNC_2H_5)_4][Pt(CN)_4] \quad (Eq.\ 4)$$

It has been found that the use of a non-ionic starting material as the cation source allows a variety of mixed metal double-complex salts to be made in one step, without contamination by tetrahaloplatinate; for example:

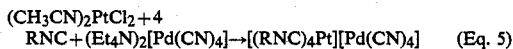

$$(CH_3CN)_2PtCl_2 + 4\ RNC + (Et_4N)_2[Pd(CN)_4] \rightarrow [(RNC)_4Pt][Pd(CN)_4] \quad (Eq.\ 5)$$

wherein R is the same definition as for $LC_6H_4$— above.

This novel method is the method of choice for the preparation of cyanometallate mixed-metal double-complex salts. Bis-acetonitrile metal dihalides are the traditional starting materials for formation of bis-isonitrile metal dihalides but have not previously been used for double-complex salt synthesis. Again, a mixture of isonitriles may be used to produce a mixture of substituted complex salts which can be used directly for most applications. Furthermore, tetraethylammonium cation can be replaced by suitable cations such as potassium, sodium and the like.

A representative list of double-complex salts provided by the invention is given in Table 1.

TABLE 1

Complexes $[(LC_6H_4NC)_4Pt][Pd(CN)_4]$ synthesized and results of vapochromism testing using methylene chloride vapors.

| Compound | L | m.p. (°C.) | Vapochromic property |
|---|---|---|---|
| 1 | H | * | no |
| 2 | p-$C_4H_9$ | * | no |
| 3 | p-$C_6H_{11}$ | 185+ | no |
| 4 | p-$C_6H_{13}$ | 131 | no |
| 5 | p-$C_7H_{15}$ | 128 | no |
| 6 | p-$C_8H_{17}$ | 122 | yes |
| 7 | p-$C_{10}H_{21}$ | 108 | yes |
| 8 | p-$C_{12}H_{25}$ | 102 | yes |
| 9 | p-$C_{14}H_{29}$ | 98 | yes |
| 10 | p-$C_4H_9$/p-$C_{10}H_{21}$ | * | no |
| 11 | m-$C_8H_{17}O$ | * | no |
| 12 | p-$C_{12}H_{25}O$ | * | no |
| 13 | p-$C_4H_9OC_5H_{10}$ | 96 | no |
| 14 | p-$C_6H_{13}OC_3H_6$ | 110 | no |
| 15 | p-$CH_3OC_{10}H_{20}$ | 104 | yes |
| 16 | p-$HCO_2C_{10}H_{20}$ | * | no |
| 17 | p-$HCO_2C_8H_{16}$ | * | no |
| 18 | p-$C_8H_{17}CH(CH_3)CH_2$ | 82 | no |

*not determined
+decomposed

All of the double-complex salts are highly colored, air-stable, and insoluble in water and organic liquids. The complexes have a limited lifetime in halogenated solvents which can cause a ligand redistribution reaction and are normally avoided. The double-complex salts do, however, disperse readily in organic liquids which allows for the preparation of coatings and composites comprising these materials.

The dispersing medium can be any non-halogenated organic liquid that does not react with the complex salt. Such liquids include any non-polar organic liquid such as hexane, toluene, benzene; moderately polar organic liquids such as diethyl ether or tetrahydrofuran; oils such as mineral oil; and polymers such as polybutene, and combinations of these liquids. The dispersing medium can be wholly or partially removed by drying.

Many of the solid vapochromic complexes are vivid pink, turning blue when exposed to organic vapors. All of the complexes of formula I are fluorescent in the visible portion of the electromagnetic spectrum. Arenyl complexes with aliphatic chains containing less than eight carbon atoms show no vapochromic effect (see Table 1, compounds 1–5), indicating the solid state behavior is linked to the length of the aliphatic chain. Electronic effects may also play a role: alkyloxyphenyl derivatives show no vapochromic effect regardless of chain length (see Table 1, compounds 11–12).

The color change induced by vapors of certain alkanes, aromatics including fluorinated aromatics, freons, and organic acids can be detected and monitored visually or by spectroscopic (absorption, emission, or fluorescence) methods. Compounds of the above type are suitable for use as monitors in vapor sensing applications requiring reversibility of the color of the monitor on exposure to or on loss of vapors from the monitor or repeated use of the same monitor.

Articles, including layered composites, of the mixed metal double-complex salts can be made which are useful as vapor monitors. A dispersion of a double-complex salt in a volatile liquid such as diethyl ether can be used to coat any inert inorganic or organic substrate (preferably porous) such as ceramics including alumina, silica, quartz, molecular sieves, or combinations thereof, etc., or for dipping paper such as filter paper. The volatile liquid can be removed by drying to provide a vaporchromic article. When paper is used, drying produces paper impregnated with the double-complex salt which can now serve as a monitor. Paper coated in this manner with the decylphenyl isonitrile mixed metal salt, $[(p\text{-}C_{10}H_{21}C_6H_4NC)_4Pt][Pd(CN)_4]$, was used to determine which vapors could be detected by this complex. Alternatively, the solid double-complex salts of the invention can be directly adhered to a support by an adherent or topcoat such as a polymer, glue, primer, etc. In all cases, at least a portion of the solid double-complex salt is not overcoated by any other material.

Table 2, below, lists the results of vapor testing and the solubility parameters (delta), where available, for the vapors tested. The solubility parameter is the Hildebrand or total solubility parameter which is a qualitative predictor of solubility or compatibility and is given in SI units of $MPa^{\frac{1}{2}}$ ($MPa = Joules\ cm^{-3}$). Tables of such parameters may be found in A. F. Barton's "CRC Handbook of Solubility Parameters and Other Cohesion Parameters"; CRC Press: Boca Raton, Fla. 1983; pp 11–12, pp 95–111.

TABLE 2

Results of Vapor Sensitivity Testing Using as Monitor [(p-C$_{10}$H$_{21}$C$_6$H$_4$NC)$_4$Pt][Pd(CN)$_4$].

| Color change observed | | No color change observed | |
|---|---|---|---|
| Compound vapor | Solubility parameter | Compound vapor | Solubility parameter |
| acetic acid | 26.5 | ammonia | |
| acetone | 19.7 | n-butanol | 28.7 |
| acetonitrile | 24.8 | 1,2 dichlorohexafluoropentene | |
| aniline | 21.1 | ethylene glycol | 34.9 |
| cyclohexane | 16.8 | formalin | |
| dichloromethane | 20.2 | formic acid | |
| m-difluorobenzene | | glycerol | 36.2 |
| p-difluorobenzene | | isooctane | 14.7 |
| dioxane | 20.7 | methanol | 29.7 |
| dodecane | 16.2 | pentane | 14.4 |
| ethanol | 26.1 | tetramethylsilane | 12.7 |
| fluorobenzene | 18.6 | triethylamine | 15.2 |
| hexane | 14.9 | water (vapor) | 48.0 |
| iodine | 28.8 | water (steam) | |
| naphthalene | 20.3 | | |
| perfluorobenzene | | | |
| perfluoronaphthalene | | | |
| toluene | 18.3 | | |
| trichlorofluoromethane | 15.5 | | |
| 1,2,4-trimethylbenzene* | 18.3 | | |
| 1,3,5-trimethylbenzene* | 18.1 | | |
| o-xylene | 18.5 | | |
| m-xylene* | 18.2 | | |
| p-xylene | 18.1 | | |

*very faint color change

From Table 2 it is apparent that there is a reasonable correlation between solubility parameter, delta, and the ability of the monitor to detect a vapor. The monitor using [(p-C$_{10}$H$_{21}$C$_6$H$_4$NC)$_4$Pt][Pd(CN)$_4$] detects vapors having a value for delta in the range of about 14.9–29.0. As a predictor of monitor efficacy, the ends of this range are less reliable than the center portion. Steric properties of the vapor molecule to be detected are a factor as well. In the xylene/trimethylbenzene series where delta is relatively constant, qualitatively any meta substitution results in only a very faint color change, i.e. for this complex a meta-substituted benzene derivative cannot be detected.

Each of the complexes is useful with a different range of solubility parameters and steric properties of the vapor molecules to be detected. The solubility parameter ranges and allowed steric tolerances need to be experimentally determined for each complex.

Water vapor does not produce a color change; in fact, the monitors made from these complexes appear to work even when wet. It is surprising that moisture does not interfere with the utility of these complexes.

As noted above, the dispersion of the invention (e.g. a polymer and double-complex salt in a suitable dispersant) can be coated as a layer on a support and then dried, or the composite can be a continuous or discontinuous layer of a double-complex salt on a support. The support can be an inorganic support such as silica, alumina, a metal, glass, ceramic, or an organic support such as paper, pressure-sensitive adhesive tape, or a polymer. In addition, the coating can be removed from the support to provide a self-supporting film.

Monitoring using the complexes of the present invention may be performed continuously, discontinuously, intermittently, or combinations thereof as required.

The complexes described may be used in applications requiring real time, visual, optical, or electronic assessment of vapors. Examples would include, but are not limited to: personal or badge type monitors, optical waveguide sensors, chemical field effect transistors, and threshold monitors.

Objects and advantages of this invention are further illustrated by the following examples, but the particular materials and amounts thereof recited in these examples, as well as other conditions and details, should not be construed to unduly limit this invention.

In the Examples:

Temperatures are reported in degrees Centigrade unless indicated otherwise. In certain cases, specific salts of compounds were used, e.g. potassium salt, but one could equally as well use a sodium or tetraalkyl ammonium, ammonium, or phosphonium salt, as long as there is sufficient solubility of the tetracyanopalladate salt for the synthetic reaction to occur in the reaction medium.

Arenyl isonitriles were synthesized from commercially available anilines which were converted to the formamides and dehydrated to isonitriles (Ugi, I., Meyr, R. *Org. Syntheses* 1961, 41, 102; Bringmann, G., Schneider, S. *Synthesis Comm.* 1983, 139–141).

Functionalized isonitriles (i.e. those that contain ether or ester linkages or chain-branching; see Table 1, compound numbers 13–18) were generally synthesized by formation of a functionalized alkylbenzene which was subsequently nitrated and reduced to the aniline. The functionalized aniline was converted to the formamide and dehydrated to the isonitrile as described above.

The formate ester of 10-(4'-isocyanophenyl)-1-decanol was prepared by nitration of 10-phenyl-1-decanol, followed by reduction of the nitro group to the amino group, then followed by formamidation and dehydration as described above.

The procedure for preparing the metal complex (CH$_3$CN)$_2$PtCl$_2$ is in the literature (Walton, R. A., *Spectrochim. Acta* 1965, 21, 1795–1801).

Use of (CH$_3$CN)$_2$PtCl$_2$ to generate cyanometallate salts is an improvement over the literature procedure because contamination of the product was avoided. (Keller, H. J., Lorentz, R. *J. Organomet. Chem.* 1975, 102, 119–122; and *Z. Naturforsch. B.* 1976, 31b, 565–568).

All novel compounds were identified by spectroscopic and/or elemental analysis. In all cases, the monitor was not in direct contact with the vapor source, only with the vapor.

EXAMPLE 1

This example illustrates the preparation of a double-complex salt in which a potassium salt of a tetracyanopalladate is used as a starting material. This method was used to prepare all compounds listed in this patent document although yields varied according to the ligand used.

[(p-C$_{10}$H$_{21}$C$_6$H$_4$NC)$_4$Pt][Pd(CN)$_4$]. To 30 ml CH$_3$CN was added 0.31 g p-C$_{10}$H$_{21}$C$_6$H$_4$NC, 0.11 g (CH$_3$CN)$_2$PtCl$_2$, 0.10 g K$_2$Pd(CN)$_4$.3H$_2$O, and 10 ml water. After approximately one hour of stirring at room temperature, the suspension was filtered, the collected solid was washed successively with acetonitrile and water and the washed solid was air-dried. The yield was 61% of an intensely pink solid, mp. 110° C.

EXAMPLE 2

This example illustrates the preparation of a salt in which a tetraalkylammonium salt of the tetracyanopalladate is used as a starting material. This method may be used to prepare all compounds listed in this patent document although yields will vary according to the ligand used.

[(p-$C_8H_{17}C_6H_4NC)_4Pt$][$Pd(CN)_4$]. To 25 ml $CH_3CN$ was added 0.28 g p-$C_8H_{17}C_6H_4NC$, 0.11 g $(CH_3CN)_2PtCl_2$, and 0.15 g [$(C_2H_5)_4N$]$_2$[$Pd(CN)_4$]·$3H_2O$. The reaction mixture was stirred at room temperature until infrared spectra showed no starting material remained. The suspension was filtered, and the collected solid was washed successively with acetonitrile and water, and air-dried. The yield was 0.20 g of an intensely pink solid, mp. 122°–123° C.

EXAMPLE 3

Vapor testing via a visually detected change in color. Response to vapors was judged visually by exposing paper monitors, impregnated with a double complex salt of this invention, to vapors. Filter paper such as Whatman #2 paper filters were dipped in a dispersion of <0.1 g of [(p-$C_{10}H_{21}C_6H_4NC)_4Pt$][$Pd(CN)_4$] in a 10 ml hexane and air dried. Samples of these monitors were used to evaluate efficacy of the monitor for the vapors of the compounds in Table 2, above. The resulting paper 'monitors' before use were vivid pink. These monitors were used to test for vapors by holding the monitors over a vessel containing the compound to be evaluated or by placing the monitor in a closed vessel with the vapor source if the vapor pressure of the source was very low (as in the case of dodecane or naphthalene). If the monitor was sensitive to the vapor the monitor changed color from pink to blue or purple.

EXAMPLE 4

Vapor testing via change in fluorescence. The detection of vapors can also be done optically using spectroscopic techniques. Either absorption or fluorescence can be monitored; a fluorescence method is described. A paper monitor prepared as described in Example 3 was placed in a closed container of dodecane. The fluorescence of [(p-$C_{10}H_{21}C_6H_4NC)_4Pt$][$Pd(CN)_4$] was measured of the resulting blue monitor by placing the monitor in the sample compartment of a fluorescence spectrometer and measuring the emission of the monitor using an excitation wavelength of 355 nm. After evaporation of adsorbed dodecane the fluorescence of the pink form of the monitor was measured. The pink form had an emission wavelength, lambda$_{max}$ of 625 nm when excited at 355 nm. Upon exposure to dodecane, the emission was reduced by 60% at this wavelength, making monitoring by fluorescence a viable method.

EXAMPLE 5

This example demonstrates one method for making vapochromic composites.

A mixture of 3.03 g silica gel (EM TM Reagents, Kieselgel TM 60, 0.04–0.063 micrometer size, VWR Scientific, San Francisco, CA), 0.04 g [p-$C_{10}H_{21}C_6H_4NC)_4Pt$][$Pd(CN)_4$], and diethyl ether was allowed to evaporate under gaseous nitrogen flow with stirring to produce a bright pink solid which retained its vapochromic behavior.

Various modifications and alterations of this invention will become apparent to those skilled in the art without departing from the scope and spirit of this invention, and it should be understood that this invention is not to be unduly limited to the illustrative embodiments set forth herein.

I claim:

1. An article comprising a substrate coated on at least one surface thereof with a continuous or discontinuous layer of a transition metal double-complex salt having a cation and an anion, said salt comprising four arenyl isonitrile ligands, at least one of which contains a long chain aliphatic group, the salt having two metal-containing complex ions, the cation being a tetrakis isonitrile platinum ion and the anion being a tetracyanopalladate ion, each of the ions having a square planar configuration, said article being useful in vapochromic monitoring application.

2. The article according to claim 1 wherein said complex salt has the formula

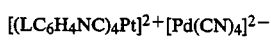

wherein $C_6H_4$ is a ring structure, and $LC_6H_4NC$ is an arenyl isonitrile ligand, wherein L is independently selected from hydrogen and aliphatic groups, with the proviso that:

for at least one L which is an aliphatic group the total number of carbon and heteroatoms in L is 8 to 20 wherein the heteroatoms are 0 to 4 unitary S, N, and O atoms, and with the proviso that:

L contains a chain of at least 6 linear catenated carbon atoms which is attached to the $C_6H_4$ ring.

3. The article according to claim 2 wherein L is an aliphatic group.

4. The article according to claim 2 wherein L contains 8 linear catenated carbon atoms.

5. The article according to claim 2 wherein L is in the para position to the isonitrile group of the arenyl isonitrile ligand.

6. The article according to claim 2 wherein the heteroatoms included in L are 1 to 4 unitary heteroatoms or heteroatom-containing divalent functional groups selected from the group consisting of

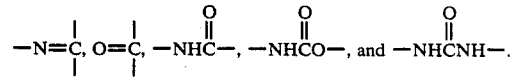

7. The article according to claim 2 wherein all L are the same aliphatic group.

8. The article according to claim 1 wherein said double-complex salt is in a dispersion coated as a continuous or discontinuous layer on at least one surface of said substrate.

9. The article according to claim 8 wherein said substrate is an inert inorganic or organic substrate.

10. The article according to claim 9 wherein said substrate is selected from the group consisting of alumina, silica, quartz, and combinations thereof.

11. The article according to claim 9 wherein said substrate is a molecular sieve.

12. The article according to claim 9 wherein said substrate is paper.

13. The article according to claim 8 wherein said dispersion comprises said double-complex salt and an organic liquid.

14. The article according to claim 13 wherein said organic liquid is a non-polar organic liquid, a polar organic liquid, a polymer, or an oil.

15. The article according to claim 14 wherein said organic liquid is wholly or partially removable to provide a dried vapochromic layer.

16. The article according to claim 15 wherein said dried vapochromic layer is partially overcoated by a topcoat.

17. The article according to claim 1 which is a vapochromic monitor.

18. The article according to claim 17 wherein said vapochromic monitor can be used repeatedly.

19. A method for monitoring an organic vapor in which a transition metal double-complex salt undergoes at least one of a color and fluorescence change in the presence of said organic vapor comprising the step of contacting an article comprising a substrate coated on at least one surface thereof with a continuous or discontinuous layer of at least one transition metal double-complex salt having a cation and an anion, said salt comprising at least one arenyl isonitrile ligand containing a long chain aliphatic group, the salt having two metal-containing complex ions, the cation being a tetrakis isonitrile platinum ion and the anion being a tetracyanopalladate ion, each of the ions having a square planar configuration, with an organic vapor for a time sufficient to effect a color change in said complex salt, wherein said organic vapor is selected from the group consisting of alkanes, aromatics and fluorinated derivatives thereof, freons, and organic acids.

20. The method according to claim 19 further comprising the step of drying and stripping said layer of transition metal double-complex salt from the substrate to provide a self-supporting film.

21. A method for monitoring an organic vapor in which the transition metal double-complex salt [(p-$C_{10}H_{21}C_6H_4NC)_4Pt$][$Pd(CN)_4$] undergoes at least one of a color and fluorescence change in the presence of an organic vapor that has a total solubility parameter value in the range of 14.9 to 29.0, said method comprising the step of:

contacting an article comprising a substrate coated on at least one surface thereof with a continuous or discontinuous layer of [p-$C_{10}H_{21}C_6H_4NC)_4Pt$][$Pd(CN)_4$] with said organic vapor for a time sufficient to effect a color change in said complex salt.

* * * * *

UNITED STATES PATENT AND TRADEMARK OFFICE
CERTIFICATE OF CORRECTION

PATENT NO. : 4,826,774
DATED : May 2, 1989
INVENTOR(S) : Colleen C. Nagel

It is certified that error appears in the above-identified patent and that said Letters Patent is hereby corrected as shown below:

ON TITLE PAGE: [54] "VAPOCHEROMIC" should read --VAPOCHROMIC--.

Col. 4, line 50, "balch" should read --Balch--.

Col. 8, line 11, "salt" should read --salts--.

Signed and Sealed this

Sixteenth Day of July, 1991

Attest:

HARRY F. MANBECK, JR.

Attesting Officer

Commissioner of Patents and Trademarks